(12) United States Patent
Lisanti et al.

(10) Patent No.: US 11,497,759 B2
(45) Date of Patent: Nov. 15, 2022

(54) REPURPOSCINS: TARGETED INHIBITORS OF MITOCHONDRIAL BIOGENESIS FOR ERADICATING CANCER STEM CELLS

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

(*) Notice: Subject to any disclaimer, the term of this patent is extended or adjusted under 35 U.S.C. 154(b) by 8 days.

(21) Appl. No.: 16/768,359

(22) PCT Filed: Nov. 29, 2018

(86) PCT No.: PCT/US2018/062956
§ 371 (c)(1),
(2) Date: May 29, 2020

(87) PCT Pub. No.: WO2019/108729
PCT Pub. Date: Jun. 6, 2019

(65) Prior Publication Data
US 2020/0360411 A1    Nov. 19, 2020

Related U.S. Application Data

(60) Provisional application No. 62/593,372, filed on Dec. 1, 2017.

(51) Int. Cl.
| | | |
|---|---|---|
| *A61K 31/7048* | (2006.01) | |
| *A61K 31/122* | (2006.01) | |
| *A61K 31/138* | (2006.01) | |
| *A61K 31/165* | (2006.01) | |
| *A61K 31/167* | (2006.01) | |
| *A61K 31/4025* | (2006.01) | |
| *A61K 31/44* | (2006.01) | |
| *A61K 31/4535* | (2006.01) | |
| *A61K 31/47* | (2006.01) | |
| *A61K 31/4709* | (2006.01) | |
| *A61K 31/506* | (2006.01) | |
| *A61K 31/65* | (2006.01) | |
| *A61K 45/06* | (2006.01) | |
| *A61K 47/12* | (2006.01) | |
| *A61K 47/24* | (2006.01) | |

(52) U.S. Cl.
CPC ........ *A61K 31/7048* (2013.01); *A61K 31/122* (2013.01); *A61K 31/138* (2013.01); *A61K 31/165* (2013.01); *A61K 31/167* (2013.01); *A61K 31/4025* (2013.01); *A61K 31/44* (2013.01); *A61K 31/4535* (2013.01); *A61K 31/47* (2013.01); *A61K 31/4709* (2013.01); *A61K 31/506* (2013.01); *A61K 31/65* (2013.01); *A61K 45/06* (2013.01); *A61K 47/12* (2013.01); *A61K 47/24* (2013.01)

(58) Field of Classification Search
CPC .............. A61K 31/7048; A61K 31/122; A61K 31/138; A61K 31/165; A61K 31/167; A61K 31/4025; A61K 31/44; A61K 31/4535; A61K 31/47; A61K 31/4709; A61K 31/506; A61K 31/65; A61K 45/06; A61K 47/12; A61K 47/24
USPC .......................................................... 514/25
See application file for complete search history.

(56) References Cited

U.S. PATENT DOCUMENTS

| | | |
|---|---|---|
| 4,599,326 A | 7/1986 | Marvola et al. |
| 2001/0002404 A1 | 5/2001 | Webb |
| 2004/0161405 A9 | 8/2004 | Rothbard et al. |
| 2014/0038886 A1 | 2/2014 | Mier et al. |
| 2016/0075726 A1 | 3/2016 | Neuzil |
| 2016/0339106 A1 | 11/2016 | Shanta |
| 2017/0014361 A1 | 1/2017 | Dhar |
| 2017/0037071 A1 | 2/2017 | Dhar et al. |

FOREIGN PATENT DOCUMENTS

| | | |
|---|---|---|
| CN | 1 706 391 | 12/2005 |
| CN | 1 837 225 A | 9/2006 |
| CN | 1 837 229 | 9/2006 |
| CN | 103 536 530 A | 1/2014 |

(Continued)

OTHER PUBLICATIONS

Ke et al. Caged Garcinia Xanthones, a Novel Chemical Scaffold with Potent Antimalarial Activity. Antimicrob Agents Chemother 61:e01220-16, 2017 (posted online: Oct. 31, 2016). https://doi.org/10.1128/AAC.01220-16. (Year: 2017).*

DeLuca et al., "Mitochondrial biogenesis is required for the anchorage-independent survival and propagation of stem-like cancer cells", Oncotarget, vol. 6, No. 17, pp. 14777-14795, Jun. 9, 2015.

Zeina et al., "Doxycycline and other Tetracyclines in the Treatement of Bone Metastasis", Anticancer Drugs. Nov. 2003, vol. 14, Issue 10, pp. 773-778. (Abstract Only).

(Continued)

*Primary Examiner* — Yih-Horng Shiao
(74) *Attorney, Agent, or Firm* — Nixon & Vanderhye, P.C.

(57) ABSTRACT

A therapeutic compound having intrinsic anti-mitochondrial properties may be chemically modified to target the compound to mitochondria, and the resulting "repurposcins" may have enhanced anti-cancer properties, among other advantageous properties. For example, a repurposcin may be used to treat and/or prevent tumor recurrence, metastasis, drug resistance, and/or radiotherapy resistance. Described herein are repurposcin compounds and pharmaceutical compositions that have been developed according to the present approach. Also described are methods for identifying and developing repurposcins, methods of using repurposcins to target cancer stem cells, and compositions for treating cancer containing one or more repurposcins as the active ingredient.

17 Claims, 11 Drawing Sheets

(56) References Cited

FOREIGN PATENT DOCUMENTS

| CN | 104 352 566 A | 2/2015 |
| CN | 105 884 633 A | 8/2016 |
| CN | 106 511 317 | 3/2017 |
| GB | 2472138 | 1/2011 |
| RU | 2 223 103 | 2/2004 |
| WO | WO 2008/145116 | 12/2008 |
| WO | 2009/006370 | 1/2009 |
| WO | WO 2019104115 A1 | 5/2019 |
| WO | WO 2019126179 A1 | 6/2019 |

OTHER PUBLICATIONS

Chen et al., "Mitochondria-targeted Drug Delivery System for Cancer Treatment", Journal of Drug Targeting, 2015, vol. 24, No. 6, pp. 1-11.

Zhang et al., Mitochondria Targeting Nano Agents in Cancer Therapeutics (Review), Oncology Letters, vol. 12, pp. 4887-4890, 2016.

Chile Opposition in Chile Application No. 201903283 date of writing Feb. 7, 2020.

Rebecca Lamb, et al., "Antibiotics that target mitochondria effectively eradicate cancer stem cells, across multiple tumor types: Treating cancer like an infectious disease", Oncotarget, Jan. 22, 2015, vol. 6, No. 7, pp. 4569-4584.

Supplemental European Search Report for EP 18 80 3298 dated Feb. 8, 2021.

Chenevert et al., "Enantioselective hydrolysis of (+/−)-chloramphenicol palmitate by hydrolases", Biorganic & Medicinal Chemistry Letters, Elsevier, Amsterdam, NL, vol. 4, No. 24, Dec. 22, 1994, pp. 2941-2944, XP026646478.

C. Roumana and G. Velrajb, "Investigation of Molecular Interactions of Myristic Acid with Antibiotic through Viscometric, Acoustic and Refractometric Studies", 2010 Second International Conference on Computer Research and Development, 2010, pp. 623-628, doi: 10.1109/ICCRD.2010.134.

IPRP for International Application No. PCT/US2018/062956 mailed Apr. 30, 2020.

Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.

International Search Report for PCT/US2018/062956, dated Jan. 30, 2019, 3 pages.

Written Opinion of the ISA for PCT/US2018/062956, dated Jan. 30, 2019, 9 pages.

Dreaden et al., "Tamoxifen-Poly(ethylene glycol)-Thiol Gold Nanoparticle Conjugates: Enhanced Potency and Selective Delivery for Breast Cancer Treatment", Bioconjugate Chemistry, vol. 20, No. 12, Dec. 2009, pp. 2247-2253.

Tomizawa et al., "Niclosamide suppresses hepatoma cell proliferation via the Wnt pathway", OncoTargets and Therapy, vol. 6, Nov. 15, 2013, pp. 1685-1693.

Skulachev et al., "Mitochondrial-targeted plastoquinone derivatives. Effect on senescence and acute age-related pathologies", Current Drug Targets, vol. 12, 2011, pp. 800-826.

Ohkawa et al., "Bovine Serum Albumin-Doxorubicin Conjugate Overcomes Multi drug Resistance in a Rat Hepatoma", Cancer Research, vol. 53, Sep. 15, 1993, pp. 423S-4242.

Ross et al., "Lipophilic Triphenylphosphonium Cations as Tools in Mitochondrial Bioenergetics and Free Radical Biology", Biochemistry, vol. 70, No. 2, 2005. pp. 222-230.

Biswas et al., "Liposomes loaded with paclitaxel and modified with Novel Triphenylphosphonium-PEG-PE Conjugate Possess Low Toxicity, Target Mitochondria and Demonstrate Enhanced Antitumor Effects in Vitro and In Vivo", Journal of Control Release, vol. 159, No. 3, May 10, 2012, pp. 393-402.

\* cited by examiner (A)

(B)

(C)

(D)

(A)

(B)

(C)

(A)

(B)

(C)

(A)

(B)

(C)

(D)

(A)

(B)

(A)

(B)

(1)

(4)

(2)

(5)

(3)

US 11,497,759 B2

REPURPOSCINS: TARGETED INHIBITORS OF MITOCHONDRIAL BIOGENESIS FOR ERADICATING CANCER STEM CELLS

FIELD

The present disclosure relates to "repurposcins," compounds having intrinsic anti-mitochondrial properties that are chemically modified to target the compounds to mitochondria, and includes methods for synthesizing repurposcins, methods of using repurposcins to target cancer stem cells, and pharmaceutical compositions for both treating cancer and reducing drug resistance in cancer cells, the pharmaceutical compositions containing one or more repurposcins as the active ingredient.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., Cell Cycle, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., Oncotarget, 5(22):11029-11037 (2014).

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used for the enrichment and purification of cancer stem-like cells from a heterogeneous population of living cells. Farnie et al., Oncotarget, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models. The inventors also demonstrated that several classes of non-toxic antibiotics could be used to halt cancer stem cell (CSC) propagation. Lamb et al., Oncotarget, 6:4569-4584 (2015). Because of the conserved evolutionary similarities between aerobic bacteria and mitochondria, certain classes of antibiotics or compounds having antibiotic activity can inhibit mitochondrial protein translation as an off-target side-effect.

SUMMARY

In view of the foregoing background, it is an object of this disclosure to demonstrate that existing compounds having intrinsic anti-mitochondrial properties can be chemically modified to target the mitochondria and thus can be used to eradicate CSCs. Such compounds may include, for example, FDA-approved pharmaceuticals, nutraceuticals, and supplements, among others. Compounds having intrinsic anti-mitochondrial properties may be modified with one or more of mitochondria-targeting signals, among other modifications, to generate a modified compound, generally referred to herein as a repurposcin, with enhanced anti-mitochondrial properties.

Described herein are examples of existing antibiotics having intrinsic anti-mitochondrial properties that have been chemically modified with one or more mitochondria-targeting signals that, as a result, have enhanced anti-cancer properties. The term "repurposcin" used herein broadly refers to a compound having intrinsic anti-mitochondrial properties that is chemically modified to target the compound to mitochondria. This relates to applicant's prior disclosure of antimitoscins, U.S. Provisional Patent Application No. 62/508,702, filed May 19, 2017, and incorporated herein by reference. It should be appreciated that antimitoscins are a class of repurposcins formed by modifying an existing antibiotic with one or more mitochondria-targeting signals as described herein.

The contemporary art considers intrinsic anti-mitochondrial activity in compounds to be an unwanted side-effect. Indeed, some potential compounds have been excluded from trials due to excessive anti-mitochondrial properties, and researchers have viewed anti-mitochondrial activity as a potential drawback. However, under the present approach, a compound's intrinsic anti-mitochondrial activity can become the basis for an entirely new therapeutic. The inventors have determined that these anti-mitochondrial properties may be harnessed and enhanced through chemical modification. As a result, compounds with intrinsic anti-mitochondrial activity may be re-purposed as novel therapeutics for, among other potential therapies, anti-cancer treatments. These compounds may bind to either the large sub-unit or the small sub-unit of the mitochondrial ribosome (or in some instances, both) and inhibit mitochondrial biogenesis. Alternatively, these compounds may bind to the inner mitochondrial membrane to block the OXPHOS pathway and thus inhibit mitochondrial metabolism. The present disclosure further describes methods of synthesizing repurposcins, methods of using repurposcins to target cancer stem cells, and pharmaceutical compositions for both treating cancer and for reducing drug resistance, the pharmaceutical compositions containing one or more repurposcins as the active ingredient.

The present disclosure may, in some embodiments, take the form of a repurposcin. Exemplar repurposcins are disclosed herein. In some embodiments, the repurposcin comprises a compound having intrinsic anti-mitochondrial properties and a mitochondria-targeting compound. In some embodiments, the compound is a member of the tetracycline family, the erthyromycin family, chloramphenicol, pyrvinium pamoate, atovaquone, and bedaquiline. The mitochondria-targeting compound may be a chemical modification to the antibiotic. In some embodiments, the mitochondria-targeting compound is at least one compound selected from the group comprising a membrane targeting signal and a mitochondria-targeting signal. In some embodiments, the membrane targeting signal is a compound selected from the group comprising palmitic acid, stearic acid, myristic acid, and oleic acid. In some embodiments, the mitochondria-targeting signal is selected from the group comprising tri-phenyl-phosphonium and guanidinium. In some embodiments, the repurposcin possesses anti-cancer activity. In some embodiments, the repurposcin binds to either or both the large sub-unit and the small sub-unit of the mitochondrial ribosome. In some embodiments, the repurposcin binds to at least one of the large sub-unit of the mitochondrial ribosome and the small sub-unit of the mitochondrial ribosome. In some embodiments, the repurposcin binds to the inner mitochondrial membrane. In some embodiments, a repurposcin possesses radiosensitizing activity, photosensitizing activity, sensitizes cancer cells to chemotherapeutic agents, sensitizes cancer cells to natural substances, and/or sensitizes cancer cells to caloric restriction. In some embodiments, the present disclosure relates to methods of treating cancer comprising administering to a patient in need thereof of a pharmaceutically effective amount of a repurposcin and a pharmaceutically acceptable carrier. In some embodiments, the present disclosure relates to a pharmaceutical composition for treating cancer containing, as the active ingredient, at least one repurposcin. In some embodiments, the pharmaceutical composition comprises a plurality of repurposcins. Embodiments of the present approach may take the form of methods of synthesizing repurposcins. Embodiments of the present approach may also take the form of improving the anti-cancer properties of an antibiotic.

The inventors analyzed phenotypic properties of CSCs that could be targeted across a wide range of cancer types, and identified a strict dependence of CSCs on mitochondrial biogenesis for the clonal expansion and survival of a CSC. Previous work by the inventors demonstrated that different classes of FDA-approved antibiotics, and in particular tetracyclines such as doxycycline and erythromycin, have an off-target effect of inhibiting mitochondrial biogenesis. As a result, such compounds have efficacy for eradicating CSCs. However, these common antibiotics were not designed to target the mitochondria, and therefore their anti-cancer efficacy can be approved. Under the present approach, existing antibiotics and other compounds having intrinsic anti-mitochondrial properties may be chemically modified to form repurposcins, to target the mitochondria, and inhibit mitochondrial biogenesis and metabolism. Some embodiments of the present approach may take the form of methods for targeting one or more therapeutic compounds to a cancer cell mitochondria, by chemically modifying the therapeutic compound with a mitochondria-targeting compound. The target cancer cell may be at least one of a CSC, an energetic cancer stem cell (eCSC), a circulating tumor cell (CTC), and a therapy-resistant cancer cell (TRCC).

Repurposcins selectively inhibit CSCs because mitochondrial biogenesis is upregulated in CSCs and is required for propagation and survival. As a result of their ability to inhibit mitochondrial biogenesis, repurposcins have enhanced anti-cancer properties.

DESCRIPTION

Figure 1:
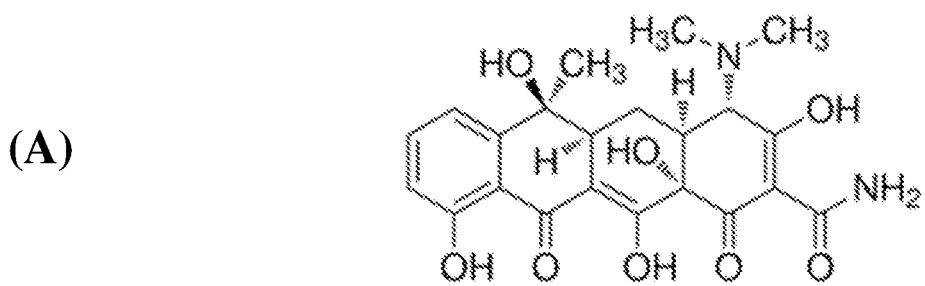
FIG. 1 illustrates members of the tetracycline family, including (A) tetracycline, (B) doxycycline, (C) tigecycline, and (D) minocycline.
Figure 1:
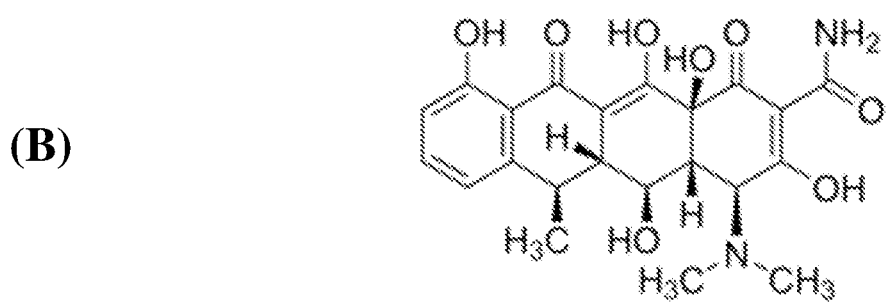
Figure 1:
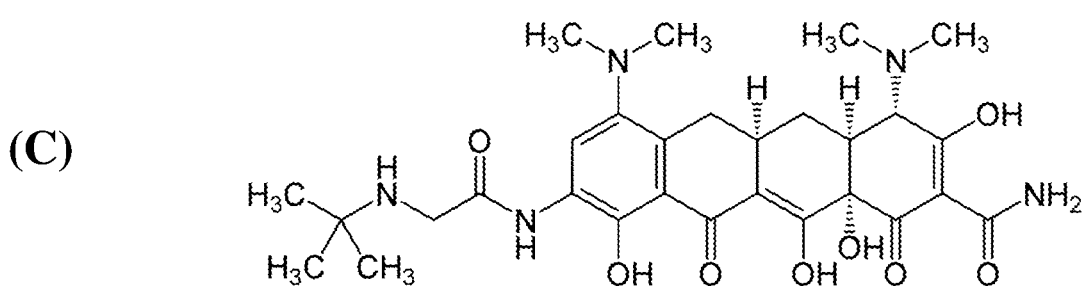
Figure 1:
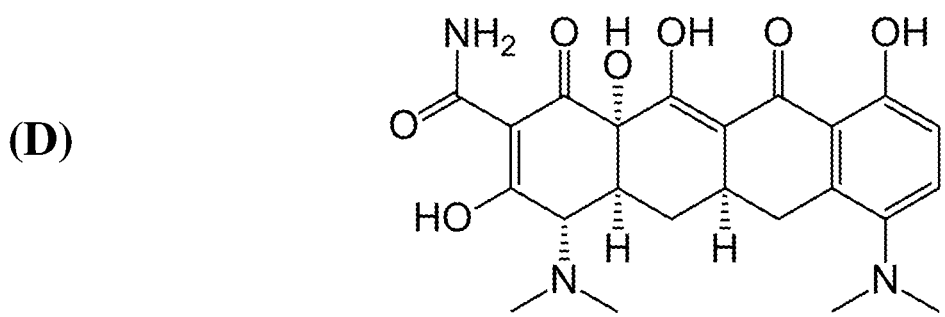

The following description illustrates embodiments of the present approach in sufficient detail to enable practice of the present approach. Although the present approach is described with reference to these specific embodiments, it should be appreciated that the present approach can be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

The mitochondria is an untapped gateway for treating a number of afflictions, ranging from cancer to bacterial and fungal infections to aging. Functional mitochondria are required for the propagation of cancer stem cells. Inhibiting mitochondrial biogenesis and metabolism in cancer cells impedes the propagation of those cells. Mitochondrial inhibitors therefore represent a new class of anti-cancer therapeutics.

As disclosed herein, numerous existing compounds having intrinsic anti-mitochondrial properties may be chemically modified with at least one mitochondria-targeting compound. In some embodiments, the compound may be one or more of berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, and fenofibrate. In some embodiments, the compound may be one or more of neomycin, puromycin, rapamycin (and its derivatives, such as everolimus), G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, clindamycin, metronidazole, linezolid, mupirocin, vancomycin, clindamycin, cephalosporin, ciprofolxacin, streptomycin, amoxicillin, and azelaic acid. The mitochondria-targeting compound may be a chemical modification to the compound, and the chemical modification may be made according to chemical synthesis methods as are known in the art. The mitochondria-targeting compound may be one of a membrane-targeting signal and a mitochondrial-ribosome targeting signal. In some embodiments, the compound having intrinsic anti-mitochondrial properties may be chemically modified with at least one membrane-targeting signal and at least one mitochondria-targeting signal. The resulting repurposcin may be used as an anti-cancer therapeutic, as well as to target bacteria and pathogenic yeast, provide anti-aging benefits, function as radiosensitizers and/or photo-sensitizers, and/or sensitize bulk cancer cells and cancer stem cells to chemotherapeutic agents, pharmaceuticals, and/or other natural substances. For example, the chemically modified therapeutic agent may also have enhanced anti-viral activity, enhanced anti-bacterial activity, and/or enhanced anti-microbial activity. Thus, embodiments of the present approach may also be used for targeting virus replication, preventing or reducing the growth of pathogenic bacteria, yeast, and parasites, overcoming drug resistance in bacteria (e.g., methicillin-resistant *Staph. aureus*, or MRSA).

Novel compounds having intrinsic anti-mitochondrial properties that are chemically modified to target the antibiotics to mitochondria, referred to herein as "repurposcins," may be formed by the addition of at least one membrane-targeting signal and/or at least one mitochondria-targeting signal to a compound, such as an FDA-approved pharmaceutical, having intrinsic anti-mitochondrial properties. Such chemical modifications increase the efficiency of the specific targeting of these compounds to the mitochondria and in particular the mitochondrial ribosome. The resulting compound, a repurposcin, has dramatically enhanced therapeutic properties, including anti-cancer properties.

As will be appreciated by those having ordinary skill in the art, the therapeutic agent may be chemically modified with a mitochondria-targeting compound in a variety of ways known in the art. For example, one or more covalent bonds may be used to chemically modify a therapeutic agent with a mitochondria-targeting compound. In some embodiments, the therapeutic agent may be linked to a mitochondria-targeting compound via chemical linkage to a terminal end of the mitochondria-targeting compound, or to an internal subunit within the mitochondria-targeting compound through a suitable linking group. The use of covalent bonds and chemical linkages are known in the art, making further description of suitable methods unnecessary in this disclosure. It should be appreciated that more than one mitochondria-targeting compound may be used.

FIGS. 1-4 provide examples of known compounds having intrinsic anti-mitochondrial properties that are chemically modified to target the compounds to mitochondria to form a repurposcin under the present approach. Antibiotics in the tetracycline family are examples of compounds having intrinsic anti-mitochondrial properties that may be chemically modified to target the compounds to mitochondria to form repurposcins having efficacy as anti-cancer therapeutics. FIG. 1 shows the chemical structures for sample tetracycline family members, including tetracycline, doxycycline, tigecycline, eravacycline, and minocycline. Each of these broad-spectrum antibiotics may be chemically modified with at least one mitochondria-targeting compound to form a repurposcin. It should be appreciated that the specific antibiotics shown are demonstrative, and that the scope of the present approach is not limited to only those structures shown. For example, other members of the tetracycline family not specifically identified herein may be used as an initial compound for forming a repurposcin. This may include, as a non-exhaustive list of examples only, chlortetracycline, oxytetracycline, demeclocycline, lymecycline, meclocycline, methacycline, rolitetracycline, chlortetracycline, omadacycline, and sarecycline. These examples are antibiotics having anti-mitochondrial properties. Other classes of compounds may be used as the starting compound to prepare a repurposcin as described herein.

Figure 2:
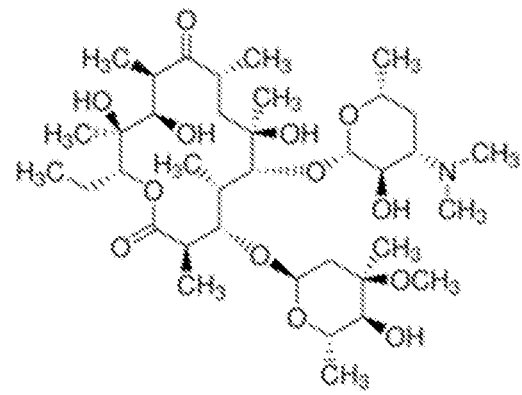
FIG. 2 illustrates members of the erythromycin family, including (A) erythromycin, (B) clarithromycin, and (C) azithromycin.
Figure 2:
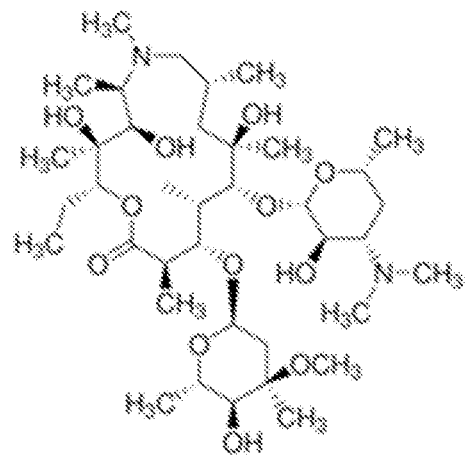
Figure 2:
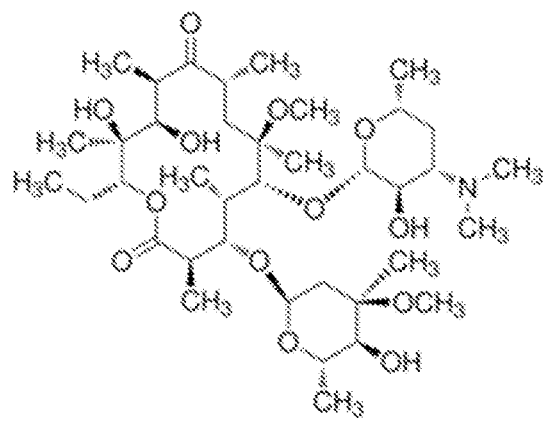

Antibiotics in the erythromycin family are additional examples of compounds having intrinsic anti-mitochondrial properties that are chemically modified to target the compounds to mitochondria to form repurposcins having efficacy as anti-cancer therapeutics. FIG. 2 shows the chemical structures for sample erythromycin family members, including erythromycin, azithromycin, roxithromycin, telithromycin, and clarithromycin. Each of these compounds may be chemically modified with at least one mitochondria-targeting compound to form a repurposcin. It should be appreciated that the specific antibiotics shown are demonstrative, and that the scope of the present approach is not limited to only those structures shown. For example, other members of the tetracycline family not specifically identified herein may be used as an initial compound for forming a repurposcin. This may include, for example, chlortetracycline, oxytetracycline, demeclocycline, lymecycline, meclocycline, methacycline, minocycline, rolitetracycline, tigecycline, omadacycline, and sarecycline, to name a few further examples.

Figure 3:
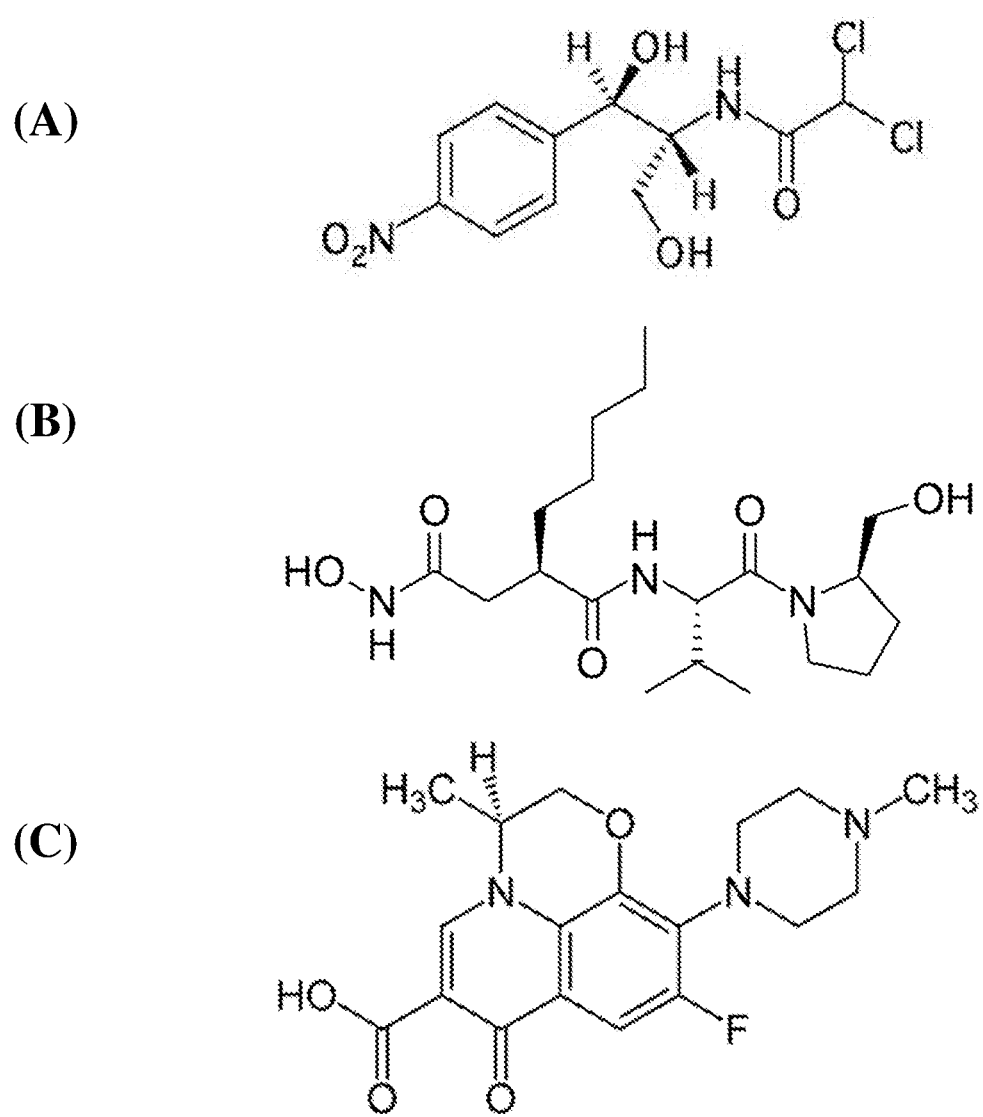
FIG. 3 illustrates other antibiotics known to inhibit the mitochondrial ribosome or mitochondrial protein translation via off-target side-effects, including (A) chloramphenicol, (B) actinonin, and (C) levofloxacin.
Figure 4:
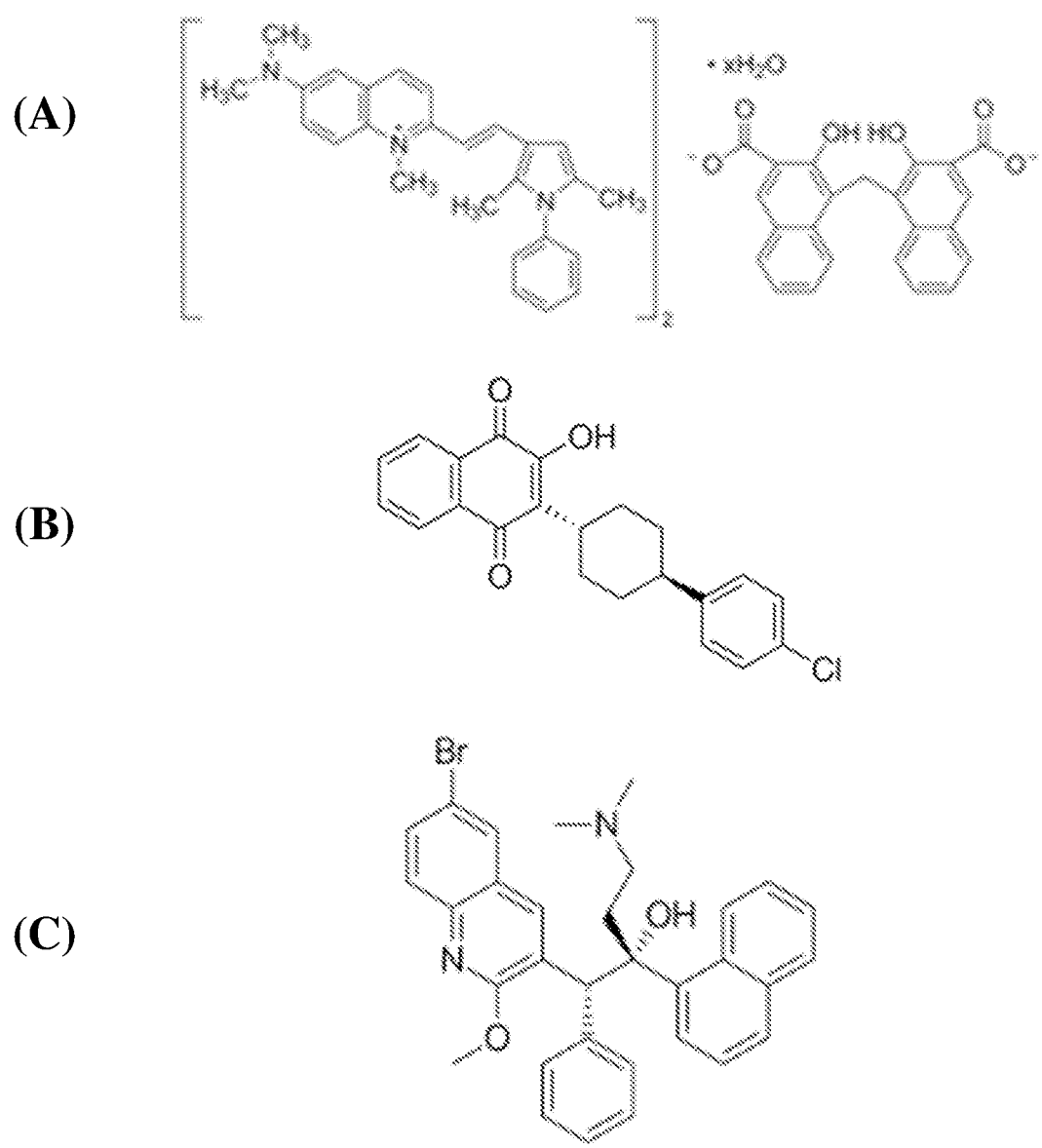
FIG. 4 illustrates other antibiotics known to inhibit the mitochondrial ribosome or mitochondrial protein translation via direct effects on mitochondrial oxygen consumption, including (A) pyrvinium pamoate, (B) atovaquone, and (C) bedaquiline.

Other known compounds having intrinsic anti-mitochondrial properties that are chemically modified to target the antibiotics to mitochondria may be repurposcins. FIG. 3 shows other antibiotics known to inhibit the mitochondrial ribosome or mitochondrial protein translation as an off-target side-effect. These examples include chloramphenicol, actinonin, and levofloxacin. Each of these compounds may be chemically modified with at least one mitochondria-targeting compound to form a repurposcin. FIG. 4 shows other compounds known to impact mitochondrial oxygen consumption by interfering with mitochondrial complexes I, II, III, IV, and/or V. These examples include pyrvinium pamoate, atovaquone, and bedaquiline. Each of these compounds may be chemically modified with at least one mitochondria-targeting compound to form a repurposcin.

Figure 5:
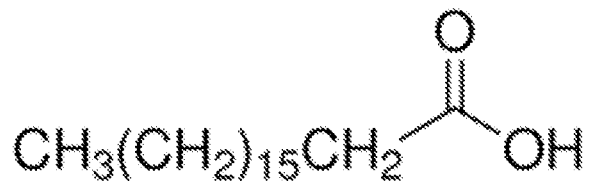
FIG. 5 shows the structures of membrane-targeting signals including the fatty acids (A) stearic acid, (B) myristic acid, (C) palmitic acid, and (D) oleic acid.
Figure 5:
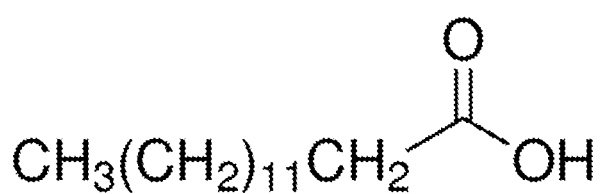
Figure 5:
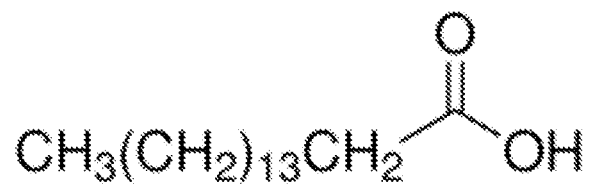
Figure 5:
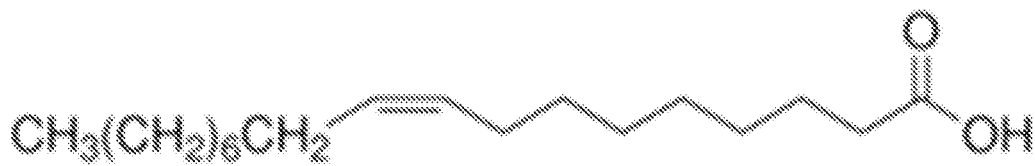
Figure 6:
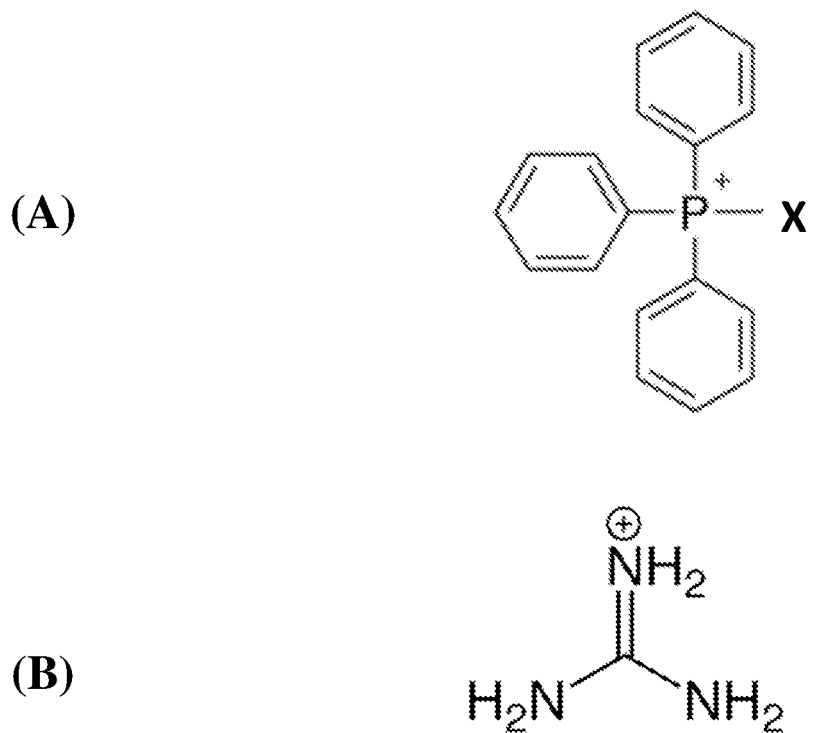
FIG. 6 shows the structures of mitochondria-targeting signals including (A) tri-phenyl-phosphonium (TPP) and (B) guanidinium.

Unlike antibiotics, repurposcins are specifically designed to target mitochondria by attachment of at least one membrane-targeting signal and/or at least one mitochondria-targeting signal. FIG. 5 provides examples of membrane-targeting signals, including fatty acids such as palmitate, stearate, myristate, and oleate. Short-chain fatty acids, i.e., fatty acids with less than six carbon atoms, may also be used as a membrane-targeting signal. Examples of short-chain fatty acids include formic acid, acetic acid, propionic acid, butyric acid, isobutyric acid, valeric acid, and isovaleric acid. The membrane-targeting signal may also be one or more medium-chain fatty acids, having 6-12 carbon atoms. It should be appreciated that this is not a comprehensive list of membrane-targeting signals, and that an unlisted membrane-targeting signal may be used without departing from the present approach. FIG. 6 provides examples of mitochondria-targeting signals, including tri-phenyl-phosphonium (TPP) and guanidinium-based moieties. Choline esters may also be used as a mitochondria-targeting signal. Tri-phenyl-phosphonium (TPP) derivative compounds, or TPP-derivatives, may also serve as mitochondria-targeting signals. The TPP-derivative compound may be, for example, 2-butene-1,4-bis-TPP; 2-chlorobenzyl-TPP; 3-methylbenzyl-TPP; 2,4-dichlorobenzyl-TPP; 1-naphthylmethyl-TPP; or p-xylylenebis-TPP. The TPP-derivative compound comprises 2-butene-1,4-bis-TPP in some preferential embodiments. In some embodiments, there may be more than one TPP-derivative. In some embodiments, the TPP-derivative compound is one or more of: derivatives of 2-butene-1,4-bis-TPP; derivatives of 2-chlorobenzyl-TPP; derivatives of 3-methylbenzyl-TPP; derivatives of 2,4-dichlorobenzyl-TPP; derivatives of 1-naphthylmethyl-TPP; and derivatives of p-xylylenebis-TPP. It should be appreciated that this is not a comprehensive list of mitochondria-targeting signals, and that an unlisted mitochondria-targeting signal may be used without departing from the present approach.

Figure 7:
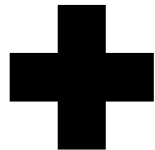
FIG. 7 shows a demonstrative method of forming a repurposcin by means of identifying a therapeutic compound and attaching (covalent or non-covalent) a membrane or mitochondria-targeting signal.
Figure 8:
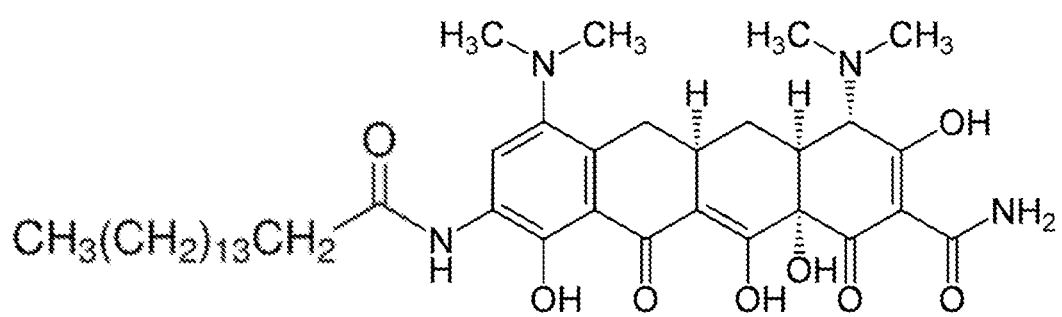
FIG. 8 shows the structures of two repurposcins, (A) an antibiotic with palmitic acid, and (B) an antibiotic with TPP.
Figure 8:
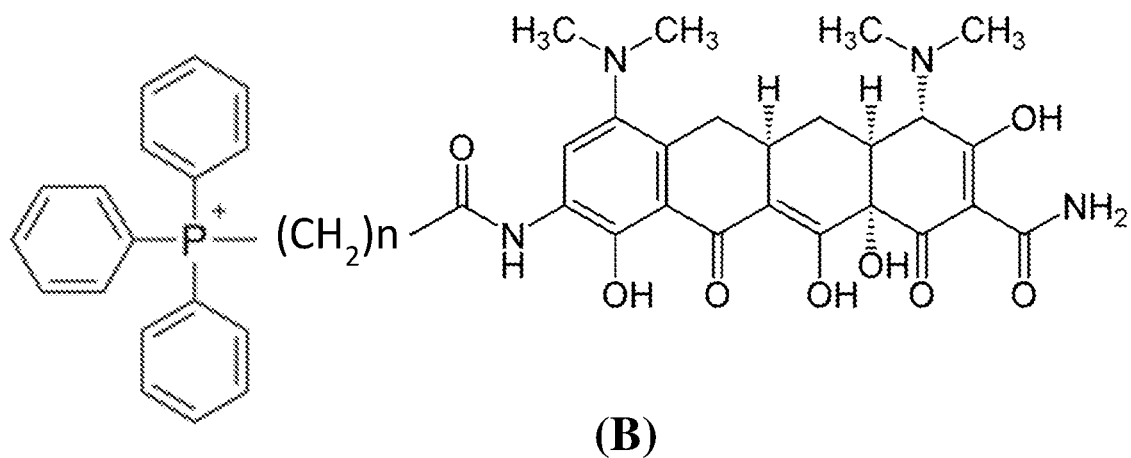

As described herein, a repurposcin may be formed by chemically modifying a compound having intrinsic anti-mitochondrial properties with at least one membrane-targeting signal and/or at least one mitochondria-targeting signal. FIG. 7 shows a method of forming a repurposcin by identifying a therapeutic compound having an intrinsic anti-mitochondrial effect (S701), and attaching (covalently or non-covalently) a membrane targeting signal or mitochondria-targeting signal (S703). FIG. 8 shows two examples of repurposcins. In these examples, the side chain of a tetracycline family member has been replaced with (A) palmitic acid and (B) a carbon-spacer-arm and TPP. It should be appreciated that the mitochondria-targeting compound(s) may be linked to the compound having intrinsic anti-mitochondrial properties in other locations without departing from the present approach.

The specific repurposcin formulas shown in FIG. 8 are examples of repurposcins formed from the exemplar antibiotics identified in FIGS. 1-4. It should be appreciated that a repurposcin may be selected for therapeutic use individually, or in combination with one or more repurposcins, and/or with other substances to enhance the efficacy of other therapeutics. For example, repurposcins formed from different compounds may be used together in a therapeutic formulation. Further, repurposcins formed from the compound but having different mitochondria-targeting compounds (such as the structures shown in FIG. 8) may be used together in a therapeutic formulation. The therapeutics may be used in the form of usual pharmaceutical compositions which may be prepared using one or more known methods. For example, a pharmaceutical composition may be prepared by using diluents or excipients such as, for example, one or more fillers, bulking agents, binders, wetting agents, disintegrating agents, surface active agents, lubricants, and the like as are known in the art. Various types of administration unit forms can be selected depending on the therapeutic purpose(s). Examples of forms for pharmaceutical compositions include, but are not limited to, tablets, pills, powders, liquids, suspensions, emulsions, granules, capsules, suppositories, injection preparations (solutions and suspensions), topical creams, and other forms as may be known in the art. For the purpose of shaping a pharmaceutical composition in the form of tablets, any excipients which are known may be used, for example carriers such as lactose, white sugar, sodium chloride, glucose, urea, starch, calcium carbonate, kaolin, cyclodextrins, crystalline cellulose, silicic acid and the like; binders such as water, ethanol, propanol, simple syrup, glucose solutions, starch solutions, gelatin solutions, carboxymethyl cellulose, shelac, methyl cellulose, potassium phosphate, polyvinylpyrrolidone, etc. Additionally, disintegrating agents such as dried starch, sodium alginate, agar powder, laminalia powder, sodium hydrogen carbonate, calcium carbonate, fatty acid esters of polyoxyethylene sorbitan, sodium laurylsulfate, monoglyceride of stearic acid, starch, lactose, etc., may be used. Disintegration inhibitors such as white sugar, stearin, coconut butter, hydrogenated oils; absorption accelerators such as quaternary ammonium base, sodium laurylsulfate, etc., may be used. Wetting agents such as glycerin, starch, and others known in the art may be used. Adsorbing agents such as, for example, starch, lactose, kaolin, bentonite, colloidal silicic acid, etc., may be used. Lubricants such as purified talc, stearates, boric acid powder, polyethylene glycol, etc., may be used. If tablets are desired, they can be further coated with the usual coating materials to make the tablets as sugar coated tablets, gelatin film coated tablets, tablets coated with enteric coatings, tablets coated with films, double layered tablets, and multi-layered tablets. Pharmaceutical compositions adapted for topical administration may be formulated as ointments, creams, suspensions, lotions, powders, solutions, pastes, gels, foams, sprays, aerosols, or oils. Such pharmaceutical compositions may include conventional additives which include, but are not limited to, preservatives, solvents to assist drug penetration, co-solvents, emollients, propellants, viscosity modifying agents (gelling agents), surfactants, and carriers.

The present approach may be used to treat and/or prevent tumor recurrence, metastasis, drug resistance, and/or radiotherapy resistance. Anti-cancer treatments often fail because the tumor recurs or metastasizes, particularly after surgery. Also, drug resistance and radiotherapy resistance are common reasons for cancer treatment failure. It is believed that CSC mitochondrial activity may be, at least in part, responsible for these causes of treatment failure. Embodiments of the present approach may be used in situations where conventional cancer therapies fail, and/or in conjunction with anti-cancer treatments to prevent failure due to tumor recurrence, metastasis, chemotherapy resistance, drug resistance, and/or radiotherapy resistance.

Repurposcins may also be used to reverse drug resistance in cancer cells. Drug resistance is thought to be based, at least in part, on increased mitochondrial function in cancer cells. In particular, cancer cells demonstrating resistance to endocrine therapies, such as tamoxifen, are expected to have increased mitochondrial function. Repurposcins inhibit mitochondrial function, and therefore are useful in reducing and, in some cases reversing, drug resistance in cancer cells. Additionally, previously generated data suggests that inhibitors of mitochondrial function that target the mitochondrial ribosome, referred to as "mitoriboscins," may be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances, such as dietary supplements and caloric restriction. Given their mitochondrial-inhibition properties, repurposcins may similarly be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances. Regarding anti-aging benefits, senescent cells are toxic to the body's normal healthy eco-system. Repurposcins may be used to selectively kill senescent cells while sparing normal tissue cells. Selectively killing senescent cells may: 1) prevent aging-associated inflammation by preventing acquisition of a senescence-associated secretory phenotype (SASP), which turns senescent fibroblasts into proinflammatory cells that have the ability to promote tumor progression; 2) facilitate tissue repair and regeneration; and/or 3) increase organismal life-span and health-span. Repurposcins may also be used to selectively kill senescent cancer cells that undergo onco-gene-induced senescence because of the onset of oncogenic stress.

In addition to antibiotics, other compounds having anti-mitochondrial activity may be modified with a membrane or mitochondria-targeting signal to have enhanced anti-cancer activity. For example, nutraceuticals and conventional chemotherapies may be modified with at least one of a membrane and a mitochondria-targeting signal to specifically target the mitochondria. The efficacy of such compounds may be increased when specifically targeting the mitochondria. Tamoxifen is one conventional chemotherapeutic agent known to have anti-mitochondrial activity. Nazarewicz et al., *Cancer Research,* 67:1282-1290 (2007). In some embodiments, tamoxifen may be modified with at least one of a membrane and a mitochondria-targeting signal to target the mitochondria. Tamoxifen belongs to a category of compounds known as selective estrogen receptor modulators (SERMs). Other SERMs, such as raloxifene, clomifene, and ethamoxytriphetol are known to have anti-mitochondrial activity and thus may be modified with at least one of a membrane and a mitochondria-targeting signal to target the mitochondria. Conventional chemotherapies that are derivatives of salicylanilide, including niclosamide, oxyclozanide, and rafoxanide are known to have anti-mitochondrial activity and thus may be modified with at least one of a membrane and a mitochondria-targeting signal to target the mitochondria. Chemotherapies that are topoisomerase inhibitors, included irinotecan, topotecan, camptothecin, lamellarin D, etoposide, teniposide, doxorubicin, daunorubicin, mitoxantrone, amsacrine, ellipticines, aurintricarboxylic acid, and HU-331, a quinolone synthesized from cannabidiol. Under the present approach, these therapeutic agents may be modified to target the mitochondria. Other chemotherapies that may be modified to target the mitochondria include multikinase inhibitors including sorafenib, regorafenib, foretinib, pazopanib, dasatinib, and sunitinib. Examples of nutraceuticals having antibiotic activity that may be modified to target the mitochondria include caffeic acid phenethyl ester (found in bee propolis), berberine, ascorbic acid (vitamin C) and other vitamins and trace minerals, polyphenols, epigallocatechin-3-gallate, resveratrol, and quercetin. It should be appreciated that this is not a comprehensive list of nutraceuticals having antibiotic activity, and that an unlisted nutraceutical may be used without departing from the present approach.

The present approach allows for methods of targeting one or more therapeutic compounds to a cancer cell mitochondria, by chemically modifying the therapeutic compound with a mitochondria-targeting compound. The target cancer cell may be at least one of a CSC, an energetic cancer stem cell (e-CSC), a circulating tumor cell (CTC, a seed cell leading to the subsequent growth of additional tumors in distant organs, a mechanism responsible for a large fraction of cancer-related deaths), and a therapy-resistant cancer cell (TRCC, a cell that has developed a resistance to one or more of chemotherapies, radiotherapies, and other common cancer treatments).

As described in Applicant's U.S. Provisional Patent Application Nos. 62/686,881, filed Jun. 19, 2018, and 62/731,561, filed Sep. 14, 2018, and incorporated by reference in their entirety, e-CSCs represent a CSC phenotype associated with proliferation. In addition to bulk cancer cells and CSCs, it should be appreciated that the present approach may be used to target a hyper-proliferative cell sub-population that the inventors refer to as e-CSCs, which show progressive increases in stemness markers (ALDH activity and mammosphere-forming activity), highly elevated mitochondrial mass, and increased glycolytic and mitochondrial activity.

Figure 9:
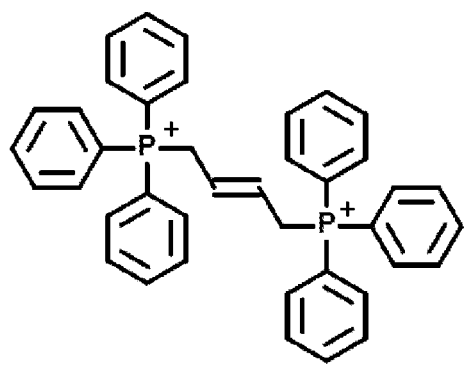
FIG. 9 illustrates the chemical structures of five TPP derivatives.
Figure 9:
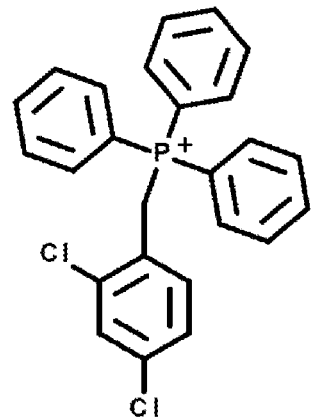
Figure 9:
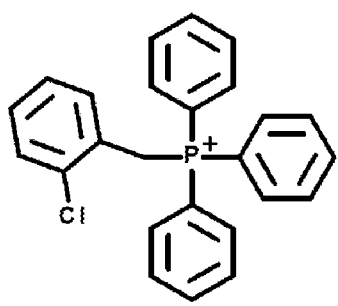
Figure 9:
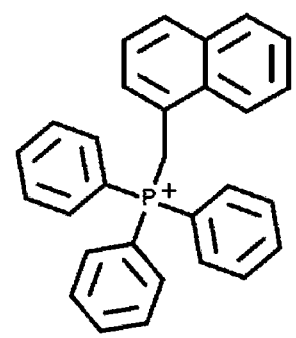
Figure 9:
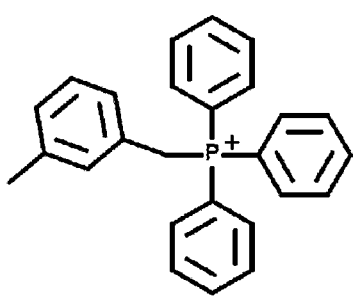

TPP and its derivatives are effective mitochondria-targeting signals for targeting "bulk" cancer cells, cancer stem cells and "normal" senescent cells (fibroblasts), without killing normal healthy cells. FIG. 9 illustrates the structure of five demonstrative TPP derivatives. These compounds are: (1) 2-butene-1,4-bis-TPP; (2) 2-chlorobenzyl-TPP; (3) 3-methylbenzyl-TPP; (4) 2,4-dichlorobenzyl-TPP; (5) 1-naphthylmethyl-TPP. It should be appreciated that the compounds shown in FIG. 9 are non-exhaustive examples.

Figure 10:
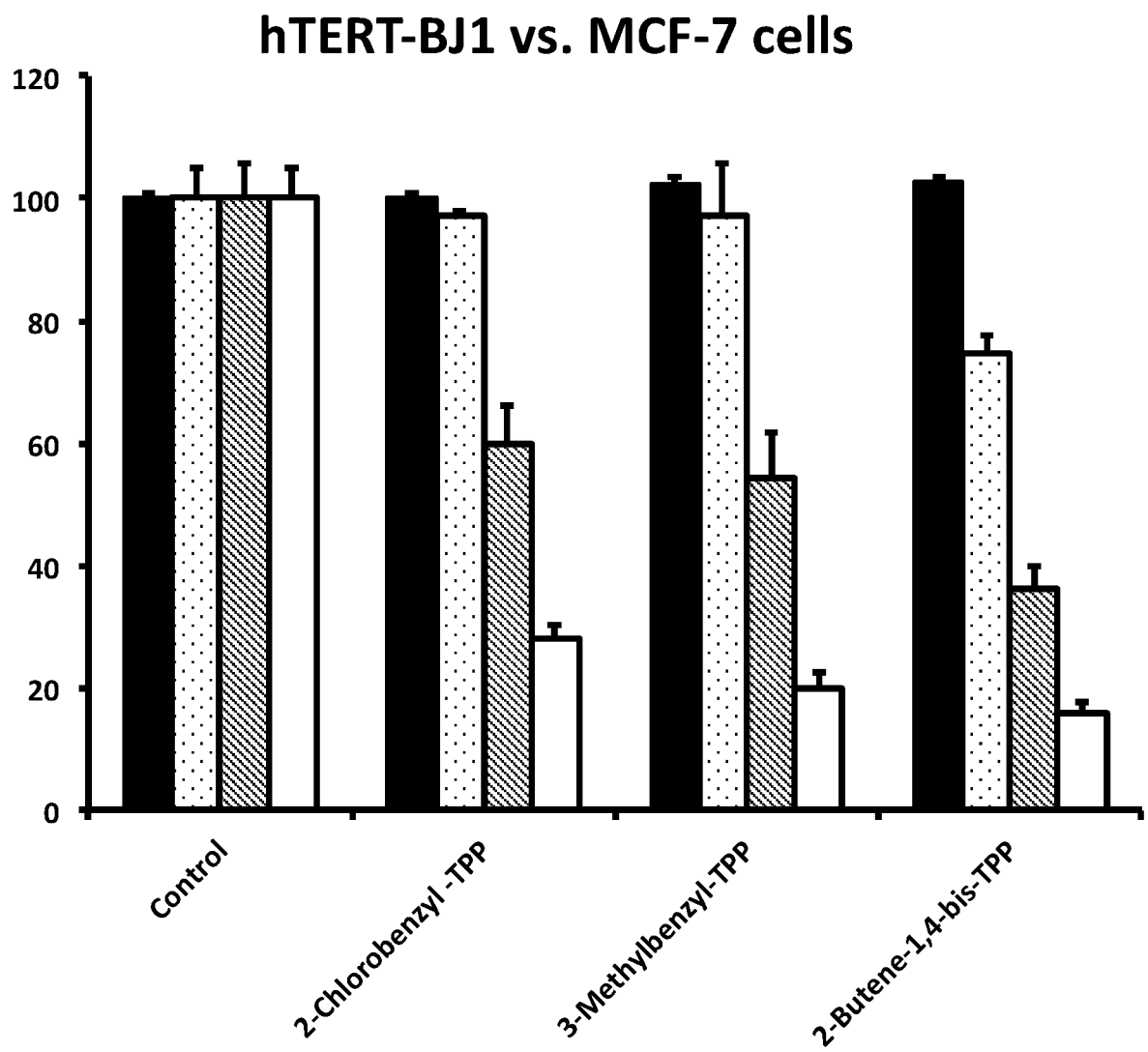
FIG. 10 shows data demonstrating the effects of TPP derivatives on cell viability and intracellular ATP levels in normal fibroblasts (hTERT-BJ1) and human breast cancer cells (MCF-7).

FIG. 10 shows data demonstrating the effects of TPP derivatives on cell viability and intracellular ATP levels in normal fibroblasts (hTERT-BJ1) and human breast cancer cells (MCF-7). Cell viability and intracellular ATP levels were determined in the same treated samples. The black bar indicates Hoechst staining (%) of hTERT-BJ1 normal human fibroblasts. The dotted bars show ATP level (%) of hTERT-BJ1 normal human fibroblasts. The lined bars show Hoechst staining (%) of MCF-7 cells. Finally, the unshaded bars show ATP level (%) of MCF-7 cells. TPP treatments at 1 μM, 72 h. Data are represented as mean+/−SEM.

Figure 11:
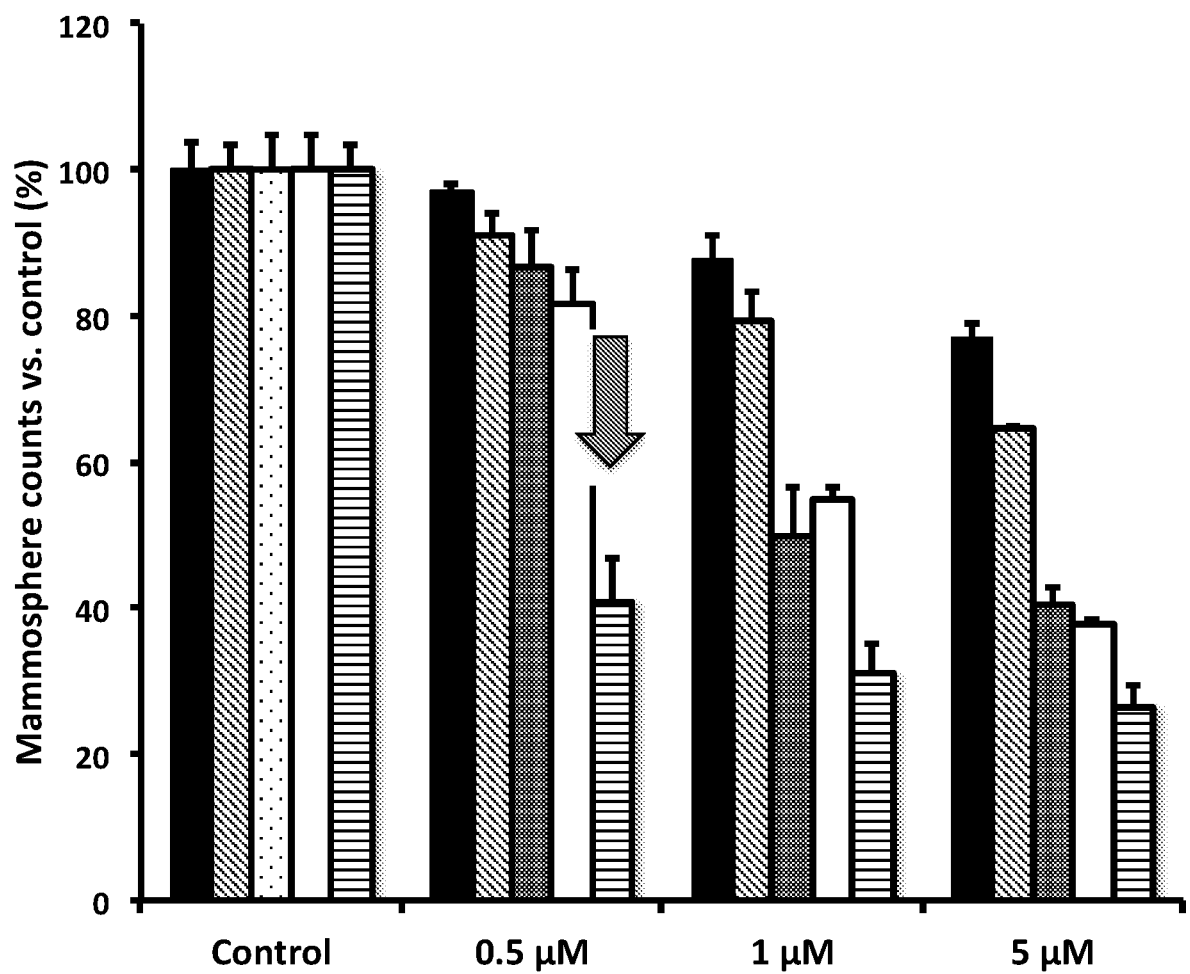
FIG. 11 shows data demonstrating inhibition of the mammosphere-forming activity of MCF-7 breast CSCs, after treatment with various TPP derivatives.

FIG. 11 shows data demonstrating inhibition of the mammosphere-forming activity of MCF-7 breast CSCs, after treatment with various TPP derivatives. The black bars show 2,4-dichlorobenzyl-TPP; the inclined bars show 1-naphthylmethyl-TPP; the dotted bars show 3-methylbenzyl-TPP; the unshaded bars show 2-chlorobenzyl-TPP; and the horizontal lined bars show 2-butene-1,4-bis-TPP. Cells used to generate these data were treated for 5 days in mammosphere media. Data are represented as mean+/−SEM. The data demonstrate that 2-butene-1,4-bis-TPP was the most effective compound for blocking CSC propagation, with an IC-50 less than 500 nM.

In view of the foregoing, it should be appreciated that the present approach may take a wide variety of forms, depending on the embodiment. For example, embodiments of the present approach may take the form of a composition, such as a pharmaceutical composition. The composition may include a therapeutic compound having intrinsic anti-mitochondrial properties, chemically modified with a mitochondria-targeting compound. The therapeutic compound may be the active ingredient, and may be present in a pharmaceutically-effective amount. The mitochondria-targeting compound may be, for example, at least one of palmitic acid, stearic acid, myristic acid, oleic acid, a short-chain fatty acid, a medium-chain fatty acid, tri-phenyl-phosphonium (TPP), and a TPP-derivative. For example, the mitochondria-targeting compound may be a TPP-derivative being at least one of 2-butene-1,4-bis-TPP; 2-chlorobenzyl-TPP; 3-methylbenzyl-TPP; 2,4-dichlorobenzyl-TPP; 1-naphthylmethyl-TPP; p-xylylenebis-TPP; a derivative of 2-butene-1,4-bis-TPP; a derivative of 2-chlorobenzyl-TPP; a derivative of 3-methylbenzyl-TPP; a derivative of 2,4- dichlorobenzyl-TPP; a derivative of 1-naphthylmethyl-TPP; and a derivative of p-xylylenebis-TPP.

The therapeutic compound may take a variety of forms. In some embodiments, the therapeutic compound may be at least one of at least one member of the tetracycline family, at least one member of the erythromycin family, chloramphenicol, pyrvinium pamoate, atovaquone, and bedaquiline. In some embodiments, the therapeutic compound may be one or more of berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, and fenofibrate. In some embodiments, the therapeutic compound may be at least one of neomycin, puromycin, rapamycin, everolimus, G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, clindamycin, metronidazole, linezolid, mupirocin, vancomycin, clindamycin, cephalosporin, ciprofolxacin, streptomycin, amoxicillin, and azelaic acid. In some embodiments, the therapeutic compound is a selective estrogen receptor modulator, such as one or more of tamoxifen, raloxifene, clomifene, and ethamoxytriphetol. In some embodiments, the therapeutic compound may be a conventional chemotherapeutic agent, such as, for example only, one or more of a derivative of salicylanilide, a topoisomerase inhibitor, and a multikinase inhibitor. The derivative of salicylanilide may be one or more of niclosamide, oxyclozanide, and rafoxanide. Examples of topoisomerase inhibitors are one or more of irinotecan, topotecan, camptothecin, lamellarin D, etoposide, teniposide, doxorubicin, daunorubicin, mitoxantrone, amsacrine, ellipticines, aurintricarboxylic acid, and HU-331. In some embodiments, the multikinase inhibitor may be one or more of sorafenib, regorafenib, foretinib, pazopanib, dasatinib, and sunitinib.

Embodiments of the present approach may possesses anti-cancer activity. In some embodiments, the composition binds to the large sub-unit of the mitochondrial ribosome. In some embodiments, the composition binds to the small sub-unit of the mitochondrial ribosome. In some embodiments, the composition possesses at least one of radiosensitizing activity and photosensitizing activity. In some embodiments, the composition sensitizes cancer cells to at least one of chemotherapeutic agents, natural substances, and caloric restriction. In some embodiments, the composition selectively kills senescent cells. In some embodiments, the composition prevents acquisition of a senescence-associated secretory phenotype. In some embodiments, the composition facilitates tissue repair and regeneration. In some embodiments, the composition increases at least one of organismal life-span and health-span.

Embodiments of the present approach may take the form of methods for synthesizing a repurposcin. A therapeutic compound having anti-cancer properties may be chemically modified with at least one of palmitic acid, stearic acid, myristic acid, oleic acid, a short-chain fatty acid, a medium-chain fatty acid, tri-phenyl-phosphonium (TPP), and a TPP-derivative. Embodiments of the present approach may also take the form of methods of treating cancer. Under the present approach, an effective amount of a composition having, as its active ingredient, a therapeutic compound having anti-cancer properties chemically modified with at least one of palmitic acid, stearic acid, myristic acid, oleic acid, a short-chain fatty acid, a medium-chain fatty acid, tri-phenyl-phosphonium (TPP), and a TPP-derivative, may be administered. Embodiments of the present approach may also take the form of methods for preventing at least one of tumor recurrence, metastasis, drug resistance, and radiotherapy resistance. An effective amount of a composition having, as its active ingredient, a therapeutic compound having anti-cancer properties chemically modified with at least one of palmitic acid, stearic acid, myristic acid, oleic acid, a short-chain fatty acid, a medium-chain fatty acid, tri-phenyl-phosphonium (TPP), and a TPP-derivative, may be administered.

Embodiments of the present approach may also take the form of methods for treating at least one of tumor recurrence, metastasis, drug resistance, and radiotherapy resistance. The method may involve administering an effective amount of a composition having, as its active ingredient, a therapeutic compound having anti-cancer properties chemically modified with at least one of palmitic acid, stearic acid, myristic acid, oleic acid, a short-chain fatty acid, a medium-chain fatty acid, tri-phenyl-phosphonium (TPP), and a TPP-derivative. In some embodiments, methods according to the present approach may be administered following a conventional cancer treatment. In other embodiments, the present approach may precede a conventional cancer treatment, such as, for example, to prevent or reduce the likelihood of recurrence, metastasis, and/or resistance. In other embodiments, the present approach may be used in conjunction with a conventional cancer treatment.

The present approach may also take the form of compositions having, as the active ingredient, a pharmaceutically-effective amount of a therapeutic compound having intrinsic anti-mitochondrial properties chemically modified with a mitochondria-targeting compound, wherein the mitochondria-targeting compound comprises at least one of palmitic acid, stearic acid, myristic acid, oleic acid, a short-chain fatty acid, a medium-chain fatty acid, tri-phenyl-phosphonium (TPP), and a TPP-derivative. It should be appreciated by those of ordinary skill in the art that a pharmaceutically-effective amount may be determined according to known methods, and may vary depending on the embodiment and the specific needs.

Embodiments of the present approach may take the form of methods for improving the anti-cancer properties of a therapeutic compound having anti-cancer properties, by chemically modifying the therapeutic compound with a mitochondria-targeting compound, wherein the mitochondria-targeting compound comprises at least one of palmitic acid, stearic acid, myristic acid, oleic acid, a short-chain fatty acid, a medium-chain fatty acid, tri-phenyl-phosphonium (TPP), and a TPP-derivative. Examples of therapeutic compounds include, but are not limited to, at least one member of the tetracycline family, at least one member of the erthyromycin family, chloramphenicol, pyrvinium pamoate, atovaquone, bedaquiline, berberine chloride, quercetin, niclosamide, acriflavinium hydrochloride, sorafenib, emetine dihydrochloride, dactinomycin, plicamycin, suloctidil, teniposide, pentamidine isethionate, daunorubicin, thioguanine, amsacrine, phenformin hydrochloride, irinotecan hydrochloride, mitomycin, hydroxyprogesterone caproate, cyclosporine, lanatoside c, mercaptopurine, quinacrine hydrochloride, fenofibrate. neomycin, puromycin, rapamycin, everolimus, G418, trovafloxacin, levofloxacin, avocatin B, clarithromycin, ciprofloxacin, spiramycin, telithromycin, norfloxacin, moxifloxacin, ofloxacin, minocycline, tetracycline, demethylchlortetracycline, clindamycin, metronidazole, linezolid, mupirocin, vancomycin, clindamycin, cephalosporin, ciprofolxacin, streptomycin, amoxicillin, and azelaic acid. The therapeutic compound may also be, for example, a selective estrogen receptor modulator, such as at least one of tamoxifen, raloxifene, clomifene, and ethamoxytriphetol. The therapeutic compound may also be, as further examples, a conventional chemotherapeutic agent, such as at least one of a derivative of salicylanilide, a topoisomerase inhibitor, and a multikinase inhibitor.

The present approach may also take the form of methods for targeting a therapeutic compound to a cancer cell mitochondria. The therapeutic compound may be chemically modified with a mitochondria-targeting compound, such as, for example, at least one of palmitic acid, stearic acid, myristic acid, oleic acid, a short-chain fatty acid, a medium-chain fatty acid, tri-phenyl-phosphonium (TPP), and a TPP-derivative. The cancer cell may be, for example, at least one of a cancer stem cell, an energetic cancer stem cell (as described herein), a circulating tumor cell, and a therapy-resistant cancer cell. The chemically modified therapeutic agent may have, in some embodiments, at least one of enhanced anti-viral activity, enhanced anti-bacterial activity, and enhanced anti-microbial activity.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention, and the claims should not be limited by these terms. These terms are only used to distinguish one element of the invention from another. Thus, a first element discussed below could be termed an element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A composition comprising, as the active ingredient, a therapeutic compound having intrinsic anti-mitochondrial properties covalently modified with a mitochondria-targeting compound, wherein the therapeutic compound is atovaquone, and the mitochondria-targeting compound comprises one of tri-phenyl-phosphonium (TPP) and a TPP-derivative.

2. The composition of claim 1, wherein the composition sensitizes cancer cells to at least one of chemotherapeutic agents, natural substances, and caloric restriction for anti-cancer activity.

3. The composition of claim 1, wherein the composition selectively kills senescent cells.

4. The composition of claim 1, wherein the composition, prevents acquisition of a senescence-associated secretory phenotype.

5. The composition of claim 1, wherein the composition, facilitates tissue repair and regeneration.

6. The composition of claim 1, wherein the composition, increases at least one of organismal life-span and health.

7. A method for synthesizing a repurposcin compound, the method comprising: covalently modifying a therapeutic compound having anti-cancer properties with one of tri-phenyl-phosphonium (TPP), and a TPP-derivative, and wherein the therapeutic compound is atovaquone.

8. A method for treating a breast cancer, the method comprising: administering an effective amount of a composition having, as an active ingredient, a therapeutic compound having anti-cancer properties covalently modified with one of tri-phenyl-phosphonium (TPP), and a TPP-derivative, and wherein the therapeutic compound is atovaquone.

9. A method for treating at least one of tumor recurrence, metastasis, drug resistance, and radiotherapy resistance of a breast cancer, the method comprising: administering an effective amount of a composition having, as an active ingredient, a therapeutic compound having anti-cancer properties covalently modified with one of tri-phenyl-phosphonium (TPP), and a TPP-derivative, and wherein the therapeutic compound is atovaquone.

10. The method of claim 9, wherein the administering is performed at least one of prior to a cancer treatment, with a cancer treatment, and following a cancer treatment.

11. A method for reversing at least one of tumor recurrence, metastasis, drug resistance, and radiotherapy resistance of a breast cancer, the method comprising: administering an effective amount of a composition having, as an active ingredient, a therapeutic compound having anti-cancer properties covalently modified with one of tri-phenyl-phosphonium (TPP), and a TPP-derivative, and wherein the therapeutic compound is atovaquone.

12. The method of claim 11, wherein the administering is performed at least one of prior to a cancer treatment, with a cancer treatment, and following a cancer treatment.

13. A composition comprising, as the active ingredient, a pharmaceutically-effective amount of a therapeutic compound having intrinsic anti-mitochondrial properties covalently modified with a mitochondria-targeting compound, and a pharmaceutically acceptable carrier, wherein the mitochondria-targeting compound comprises one of tri-phenyl-phosphonium (TPP) and a TPP-derivative, and wherein the therapeutic compound is atovaquone.

14. A method for targeting a therapeutic compound to mitochondria of a cancer cell, the method comprising: providing the therapeutic compound covalently modified with a mitochondria-targeting compound, wherein the mitochondria-targeting compound is selected from the group consisting of tri-phenyl-phosphonium (TPP) and a TPP-derivative, and wherein the therapeutic compound is atovaquone.

15. The method of claim 14, wherein the cancer cell comprises at least one of a cancer stem cell, an energetic cancer stem cell, a circulating tumor cell, and a therapy-resistant cancer cell.

16. The composition of claim 1, wherein the mitochondria-targeting compound comprises TPP.

17. The composition of claim 13, wherein the mitochondria-targeting compound comprises TPP.

* * * * *